United States Patent

Regel et al.

[11] 4,251,540
[45] Feb. 17, 1981

[54] COMBATING CROP DAMAGING FUNGI WITH α-(4-BIPHENYLYL)-BENZYL-AZOLIUM SALTS

[75] Inventors: Erik Regel; Wilfried Draber; Karl H. Büchel, all of Wuppertal; Peter Kraus, Cologne; Wilhelm Brandes, Leichlingen, all of Fed. Rep. of Germany

[73] Assignee: Bayer Aktiengesellschaft, Leverkusen, Fed. Rep. of Germany

[21] Appl. No.: 73,171

[22] Filed: Sep. 6, 1979

Related U.S. Application Data

[63] Continuation of Ser. No. 885,247, Mar. 10, 1978, abandoned.

[30] Foreign Application Priority Data

Mar. 31, 1977 [DE] Fed. Rep. of Germany ....... 2714290

[51] Int. Cl.³ .................. A01N 43/50; A01N 43/56
[52] U.S. Cl. ................. 424/273 R; 424/269
[58] Field of Search ................. 424/269, 273 R

[56] References Cited

U.S. PATENT DOCUMENTS

| 3,658,813 | 4/1972 | Godefroi | 548/341 |
| 3,711,502 | 1/1973 | Buchel | 548/345 |
| 3,836,540 | 9/1974 | Van Der Stetti | 260/309 |
| 3,991,202 | 11/1976 | Janssen et al. | 424/273 |
| 3,992,397 | 11/1976 | Winkelmann et al. | 424/269 |
| 4,079,143 | 3/1978 | Balasvbramanyan et al. | 424/269 |

FOREIGN PATENT DOCUMENTS 1795249 12/1971 Fed. Rep. of Germany ........... 424/273

OTHER PUBLICATIONS

Chemical Abstracts 85:160,095L (1976).

Primary Examiner—Leonard Schenkman
Attorney, Agent, or Firm—Sprung, Felfe, Horn, Lynch & Kramer

[57] ABSTRACT

α-(4-Biphenylyl)-benzyl-azolium salts of the formula

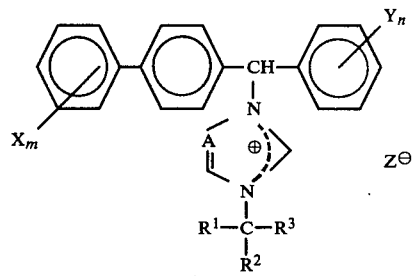

in which
A is CH or N,
R¹ and R² each independently is hydrogen, alkyl or optionally substituted phenyl,
R³ is hydrogen, alkyl or optionally substituted phenyl, phenylalkyl, phenylcarbonyl or phenylcarbonylalkyl,
m is 0, 1, 2, 3, 4 or 5,
X each independently is halogen, alkyl, halogenoalkyl, alkoxy, alkylthio, nitro or cyano,
n is 0, 1, 2, 3, 4 or 5,
Y each independently is halogen, alkyl, halogenoalkyl, alkoxy, alkylthio, nitro, cyano or phenyl which is optionally substituted by halogen, alkyl, halogenoalkyl, alkoxy, alkylthio, nitro or cyano, and
Z is the anion of an inorganic or organic acid,
are used to combat fungi.

5 Claims, No Drawings

COMBATING CROP DAMAGING FUNGI WITH α-(4-BIPHENYLYL)-BENZYL-AZOLIUM SALTS

This is a continuation of application Ser. No. 885,247, filed Mar. 10, 1978, now abandoned.

The present invention relates to the use, as fungicides, of certain α-(4-biphenylyl)-benzyl-azolium salts.

It has already been disclosed that certain trityl-1,2,4-triazoles, such as triphenyl-(1,2,4-triazol-1-yl)-methane, have a good fungicidal activity (see German Offenlegungsschrift (German Published Specification) No. 1,795,249), as have certain 1-phenylethyl-imidazolium salts, such as 1-[2,4-dichloro-β-(2,4-dichlorobenzyloxy)-phenylethyl]-3-(4-fluorobenzoylmethyl)-imidazolium chloride (see German Offenlegungsschrift (German Published Specification) No. 2,504,144). However, the action of these azole derivatives is not always completely satisfactory, especially when low application amounts and concentrations are used.

It has been found that the α-(4-biphenylyl)-benzylazolium salts of the general formula

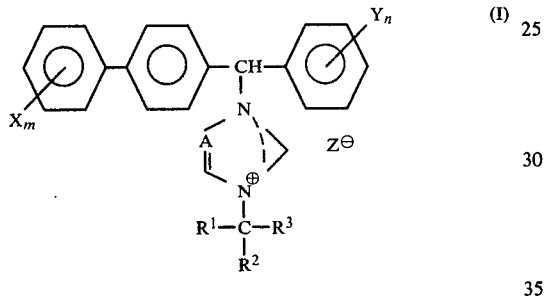

in which
A represents the CH group or a N atom,
$R^1$ and $R^2$, which may be identical or different, each represent hydrogen, alkyl or optionally substituted phenyl,
$R^3$ represents hydrogen, alkyl or optionally substituted phenyl, phenylalkyl, phenylcarbonyl or phenylcarbonylalkyl,
m is 0, 1, 2, 3, 4 or 5,
X represents halogen, alkyl, halogenoalkyl, alkoxy, alkylthio, nitro or cyano, the X's being selected independently of one another when m is 2 or more,
n is 0, 1, 2, 3, 4 or 5,
Y represents halogen, alkyl, halogenoalkyl, alkoxy, alkylthio, nitro, cyano or phenyl which is optionally substituted by halogen, alkyl, halogenoalkyl, alkoxy, alkylthio, nitro or cyano, with the Y's being selected independently of one another when n is 2 or more, and
Z represents the anion of an inorganic or organic acid,
have powerful fungicidal properties.

Preferably, each X represents fluorine, chlorine, bromine, alkyl with 1 to 6 (especially with up to 4) carbon atoms (methyl, ethyl, isopropyl and tert.-butyl being mentioned as examples of such alkyl groups), halogenoalkyl with 1 to 4 carbon atoms and up to 5 halogen atoms (especially with 1 or 2 carbon atoms and up to 3 identical or different halogen atoms selected from fluorine and chlorine, trifluoromethyl being mentioned as an example of such halogenoalkyl groups), alkoxy or alkylthio each with 1 to 4 carbon atoms (methoxy, ethoxy, methylthio or ethylthio being mentioned as examples of such alkoxy and alkylthio groups), nitro or cyano;

each Y represents fluorine, chlorine, bromine, alkyl with 1 to 6 (especially with up to 4) carbon atoms, halogenoalkyl with 1 to 4 carbon atoms and up to 5 halogen atoms (especially with 1 or 2 carbon atoms and up to 3 identical or different halogen atoms selected from fluorine and chlorine), alkoxy or alkylthio each with 1 to 4 carbon atoms (for example methoxy, ethoxy, methylthio or ethylthio), nitro, cyano or phenyl which is optionally substituted by fluorine, chlorine, bromine, alkyl with 1 to 6 (especially with up to 4) carbon atoms, halogenoalkyl with 1 to 4 carbon atoms and up to 5 halogen atoms (especially with 1 or 2 carbon atoms and up to 3 identical or different halogen atoms selected from fluorine and chlorine), alkoxy or alkylthio each with 1 to 4 carbon atoms, nitro or cyano;

$R^1$ and $R^2$, which may be identical or different, each represent hydrogen, straight-chain or branched alkyl with 1 to 4 carbon atoms or phenyl which is optionally substituted by fluorine, chlorine, bromine, alkyl with 1 to 6 (especially with up to 4) carbon atoms, halogenoalkyl with 1 to 4 carbon atoms and up to 5 halogen atoms (especially with 1 or 2 carbon atoms and up to 3 identical or different halogen atoms selected from fluorine and chlorine), alkoxy or alkylthio each with 1 to 4 carbon atoms, nitro or cyano;

$R^3$ represents hydrogen, straight-chain or branched alkyl with 1 to 4 carbon atoms or phenyl, phenylalkyl with 1 to 4 carbon atoms in the alkyl part, phenylcarbonyl or phenylcarbonylalkyl with 1 to 4 carbon atoms in the alkyl part, the last four groups being optionally substituted by fluorine, chlorine, bromine, alkyl with 1 to 6 (especially with up to 4) carbon atoms, halogenoalkyl with 1 to 4 carbon atoms and up to 5 halogen atoms (especially with 1 or 2 carbon atoms and up to 3 identical or different halogen atoms selected from fluorine and chlorine), alkoxy or alkylthio each with 1 to 4 carbon atoms, nitro, cyano or phenyl which is itself optionally substituted by fluorine, chlorine, bromine, alkyl with 1 to 6 (especially with up to 4) carbon atoms, halogenoalkyl with 1 to 4 carbon atoms and up to 5 halogen atoms (especially with 1 or 2 carbon atoms and up to 3 identical or different halogen atoms selected from fluorine and chlorine), alkoxy or alkylthio each with 1 to 4 carbon atoms, nitro or cyano;

m and n each represent 0, 1, 2 or 3; and
$Z^\ominus$ represents a fluoride, chloride, bromide, iodide, nitrate, sulphate, phosphate, acetate, propionate, glycolate, lactate, malonate, succinate, maleate, fumarate, tartrate, citrate, benzoate, methylsulphonate, ethylsulphonate, p-toluenesulphonate, benzenesulphonate or salicylate anion.

Surprisingly, the α-(4-biphenylyl)-benzyl-azolium salts which can be used according to the invention exhibit a better fungicidal action than the azole derivatives triphenyl-(1,2,4-triazol-1-yl)methane and 1-[2,4-dichloro-β-(2,4-dichlorobenzyloxy)-phenylethyl]-3-(4-fluorobenzoylmethyl)-imidazolium chloride, which are known from the state of the art and are related compounds chemically and from the point of view of their action. The active compounds according to the invention thus represent an enrichment of the art.

Examples of particularly active compounds to be used according to the invention are the following: 1-[α-(4-biphenylyl)-benzyl]-3-(4-biphenylyl-methyl)-imidazolium chloride, 1-[α-(4-biphenylyl)-benzyl]-3-diphenylmethyl-imidazolium chloride, 1-[α-(4'-chloro-4-biphenylyl)-benzyl]-3-(4-chlorophenyl-diphenylmethyl)-imidazolium chloride, 1,3-bis-[α-(4'-chloro-4-biphenylyl)-benzyl]-imidazolium chloride, 1-[α-(4-biphenylyl)-benzyl]-3-(2,4-dichlorophenyl-diphenylmethyl)-imidazolium chloride, 1-[α-(4-biphenylyl)-benzyl]-3-(benzoyl-phenyl-methyl)-imidazolium chloride, 1-[α-(4-biphenylyl)-benzyl]-3-[tris-(4-chlorophenyl)-methyl]-imidazolium chloride, 1-[α-(4-biphenylyl)-benzyl]-3-(4-biphenylyl-methyl)-imidazolium bromide, 1-[α-(4-biphenylyl)-benzyl]-3-diphenylmethyl-imidazolium bromide, 1-[α-(4-biphenylyl)-benzyl]-4-(4-biphenylyl-methyl)-1,2,4-triazolium chloride and 1-[α-(4-biphenylyl)-benzyl]-4-diphenylmethyl-1,2,4-triazolium chloride. Further compounds are mentioned in the preparative examples given later in this text.

The compounds to be used according to the invention have not yet been described in the literature. However, they are the subject of U.S. patent application Ser. No. 833,630 of Sept. 15, 1977. They can be prepared by the process described there, by reacting 1-(α-biphenylyl-benzyl)-azoles of the general formula

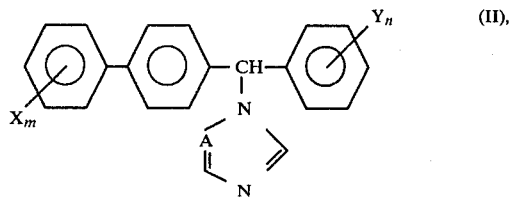

in which A, X, Y, m and n have the meanings stated above, with halides of the general formula

in which $R^1$, $R^2$ and $R^3$ have the meanings stated above and Hal represents halogen, in the presence of a polar solvent, such as, for example, acetonitrile, at temperatures between 0° and 120° C., preferably at from 20° to 90° C., and optionally replacing the halide in the resulting azolium halides by another anion in a manner which is in itself known (see German Offenlegungsschrift (German Published Specification) No. 2,504,114), by converting the α-(4-biphenylyl)-benzyl-azolium halides of the formula (I) into the corresponding azolium hydroxides, for example by means of a base or an anion exchanger, and subsequently reacting the azolium hydroxides with a corresponding acid. The compounds of the formula (I) are isolated in the customary manner. In some cases it proves to be advantageous to employ, instead of the halides of the formula (III), corresponding esters, which are obtained by reacting the appropriate alcohols with the appropriate acids.

The 1-[α-(4-biphenylyl)-benzyl]-azoles of the formula (II) to be used as starting substances are either known from German Offenlegungsschrift (German Published Specification) No. 2,461,406, or can be prepared by the processes indicated therein. They are obtained, for example, when the corresponding 1-[α-(4-biphenylyl)-benzyl]-carbinols are reacted with thionyl-bis-azoles in the presence of a solvent, for example acetonitrile, at temperatures between 0° and 100° C., or when the corresponding 1-[α-(4-biphenylyl)-benzyl] halides are reacted with azoles, optionally in the presence of an acid-binding agent, for example an excess of azole, and optionally in the presence of a solvent, for example acetonitrile, at temperatures between 80° and 120° C. (see also the preparative examples given later in this text).

The halides of the formula (III) which are also required as starting substances are compounds of organic chemistry which are known generally, and they can be obtained in a manner which is generally known and customary.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seedborne pathogens. They display a particularly good activity against parasitic fungi on above-ground parts of plants.

As plant protection agents, the active compounds of the formula (I) can be used with particularly good success for combating species of Venturia, for example for combating apple scab (*Fusicladium dendriticum*) and grey mould blight (Botryis), and against cereal diseases, for example powdery mildew of cereals.

As plant protection agents, the compounds according to the invention can be used for the treatment of soil, for the treatment of seed and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylene or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention can be present in the formulations as a mixture with other active compounds, such as fungicides, insecticides, acaricides, nematicides, herbicides, bird repellents, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001 percent.

For the treatment of seed, amounts of active compound of 0.001 to 50 g., preferably 0.01 to 10 g, are generally employed per kilogram of seed.

At somewhat higher concentrations, growth-regulating properties are also displayed.

The present invention further provides crops protected from damage by fungi by being grown in areas in which immediately prior to and/or during the time of the growing a compound of the formula (I) was applied alone or in admixture with a diluent or carrier.

It will be seen that the usual methods of providing a harvested crop may be improved by the present invention.

The following examples illustrate the preparation of the active compounds:

EXAMPLE 1

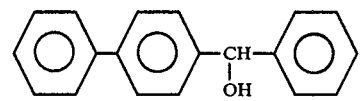
(a)

38.8 g (0.15 mol) of 4-phenyl-benzophenone were dissolved in 200 ml of ethanol, and 3 g (0.075 mol) of sodium borohydride were added. After heating the mixture under reflux for 15 hours, the cooled reaction mixture was hydrolyzed with water containing a small proportion of hydrochloric acid. The solid material thereby formed was purified by recrystallization from ethanol. This gave 36 g (89% of theory) of 4-biphenyl-phenyl-carbinol of melting point 72°–73° C.

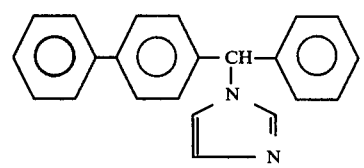
(b)

13.6 g (0.1 mol) of imidazole were dissolved in 150 ml of acetonitrile, and 3.5 ml of thionyl chloride were added at 10° C. 13 g (0.05 mol) of 4-biphenyl-phenyl-carbinol were added to the solution of thionyl-bis-imidazole thus obtained. After the mixture had stood for 15 hours at room temperature, the solvent was removed by distilling off in vacuo. The residue was taken up in chloroform and washed with water. The organic phase was separated off, dried over sodium sulphate and filtered and the solvent was distilled off from the filtrate in vacuo. The oily residue was dissolved in ethyl acetate and the solution was freed from insoluble, resinous constituents by filtration. The solvent was again distilled off in vacuo and the residue was purified by recrystallization from acetonitrile. This gave 8.7 g (56% of theory) of 1-[α-(4-biphenylyl)-benzyl]-imidazole of melting point 142° C.

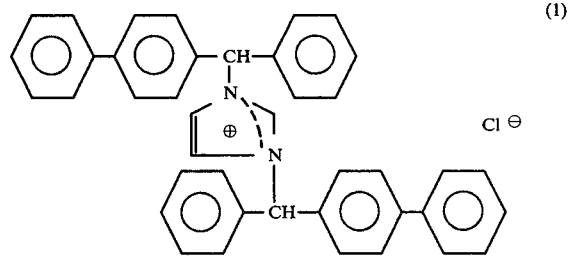
(1)

31 g (0.1 mol) of 1-[α-(4-biphenylyl)-benzyl]-imidazole and 27.9 g (0.1 mol) of α-biphenylyl-benzyl chloride were suspended in 200 ml of acetonitrile. The suspension was heated under reflux for 18 hours. The reaction mixture was then concentrated by distilling off the solvent, and the residue was heated under reflux in 500 ml of toluene. The oil thereby formed was separated off and was crystallised by trituration with diisopropyl ether. This gave 36 g (62% of theory) of 1,3-bis-[α-(4-biphenylyl)-benzyl]imidazolium chloride of melting point 150° C. (decomposition).

EXAMPLE 2

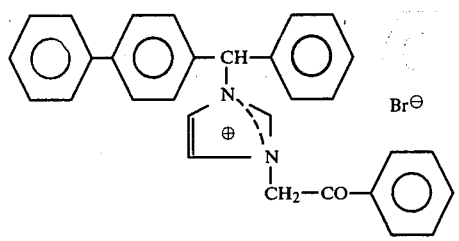
(2)

15.1 g (0.05 mol) of 1-[α-(4-biphenylyl)-benzyl]-imidazole and 10 g (0.05 mol) of ω-bromoacetophenone were suspended in 500 ml of acetonitrile. After stirring the suspension for 15 hours at room temperature, the clear solution which had formed was concentrated to about 50 ml. The crystals which thereby separated out were filtered off and dried. This gave 21 g (82.5% of theory) of 1-[α-(4-biphenylyl)-benzyl]-3-benzoylmethyl-imidazolium bromide of melting point 210° C. (decomposition).

EXAMPLE 3

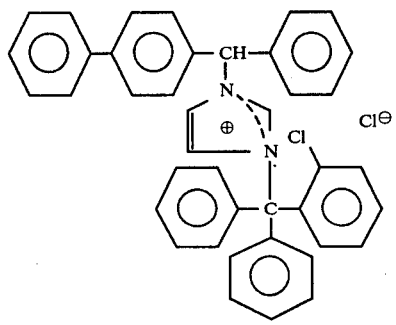
(3)

15.1 g (0.05 mol) of 1-[α-(4-biphenylyl)-benzyl]-imidazole and 15.2 g (0.05 mol) of 2-chlorophenyl-diphenylmethyl chloride were suspended in 400 ml of acetonitrile and the suspension was heated to 80° C. for 24 hours. The mixture was then filtered, and the filtrate was concentrated by distilling off the solvent. After trituration with ether, the residue crystallised. This gave 13 g (42% of theory) of 1-[α-(4-biphenylyl)-benzyl]-3-(2-chlorophenyl-diphenylmethyl)-imidazolium chloride of melting point 140° C. (decomposition).

EXAMPLE 4

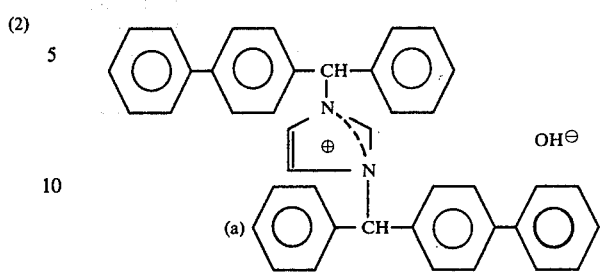
(a)

A solution of 140 g (0.238 mol) of 1,3-bis-[α-(4-biphenylyl)-benzyl]-imidazolium chloride (Example 1) in 1,500 ml of ethanol was passed through a 150 cm long glass column, filled with 1,000 g of Lewatit M 504 (an ion exchanger consisting of polystyrene with quaternary ammonium groups), after the ion exchanger had been converted into the OH form by treatment with 1 N sodium hydroxide solution. The column was rinsed with ethanol, and the eluate was freed from solvent in vacuo. This gave 120.2 g (89% of theory) of 1,3-bis-[α-(4-biphenylyl)-benzyl]-imidazolium hydroxide of melting point 82° C.

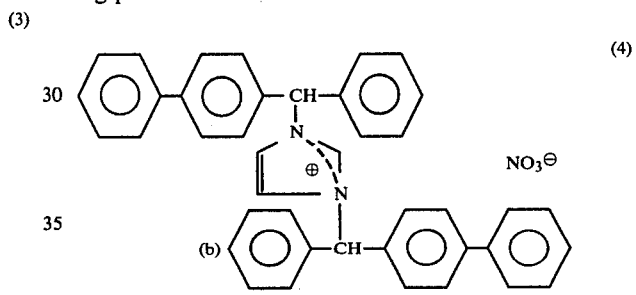
(b)
(4)

(via replacement of the anion)

1 ml of 96% strength nitric acid was added to a solution of 10 g (0.0175 mol) of 1,3-bis-[α-(4-biphenylyl)benzyl]-imidazolium hydroxide in 100 ml of acetonitrile. After heating the mixture to 80° C. for 4 hours, the solvent was distilled off in vacuo. After standing for several days and trituration with diisopropyl ether, the oily residue crystallised. This gave 10.5 g (97% of theory) of 1,3-bis-[α-(4-biphenylyl)-benzyl]-imidazolium nitrate of melting point 102° C.

The compounds of Table 1 which follow were obtained analogously to Examples 1 to 3.

TABLE 1

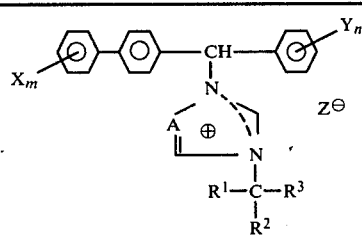
(I)

| Compound | A | R¹ | R² | R³ | $X_m$ | $Y_n$ | Z | Melting point (°C.) (decomposition) |
|---|---|---|---|---|---|---|---|---|
| 5 | CH | Cl—⌬—NO₂ | | H | —⌬—⌬— | — | 4-Cl, 3-NO₂ | Cl | 60 |

TABLE 1-continued (I) General structure shown with Xm-phenyl-phenyl-CH(-phenyl-Yn)-N-linked imidazolium ring bearing A, R1, R2, R3 and counter-ion Z⊖.

| Compound | A | R¹ | R² | R³ | $X_m$ | $Y_n$ | Z | Melting point (°C.) (decomposition) |
|---|---|---|---|---|---|---|---|---|
| 6 | CH | NO₂-phenyl- | H | -biphenyl | — | 3-NO₂ | Cl | 70 |
| 7 | CH | H | H | —CO—phenyl—Cl | — | — | Cl | 150 |
| 8 | CH | H | H | —CO—phenyl—Cl | — | — | Br | 170 |
| 9 | CH | 2,5-Cl₂-phenyl- | H | -biphenyl | — | 2,5-CL₂ | Cl | 200 |
| 10 | CH | H | H | -phenyl | — | — | Cl | 150 |
| 11 | N | -phenyl | H | -biphenyl | — | — | Cl | 164 |
| 12 | CH | -phenyl | H | -biphenyl | — | — | HSO₄ | 110 |
| 13 | CH | -phenyl | H | -biphenyl | — | — | H₂PO₄ | 120 |
| 14 | CH | -phenyl | H | -biphenyl | — | — | Acetate | 86 |
| 15 | CH | -phenyl | H | -biphenyl | — | — | Tartrate | 72 |
| 16 | CH | -phenyl | H | -biphenyl | — | — | Citrate | 105 |
| 17 | CH | -phenyl | N -phenyl | — | — | Cl | 152-156 |

The fungicidal activity of the compounds of this invention is illustrated by the following examples wherein the compounds according to the present invention are each identified by the number (given in brackets) from the preparative examples.

The known comparison compounds are identified as follows:

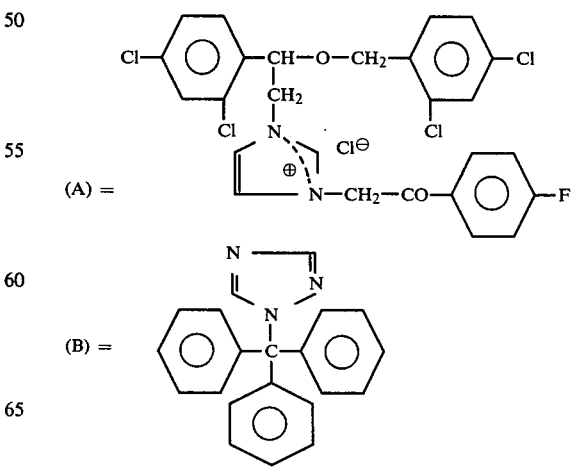

(A) = [structure shown]

(B) = [structure shown]

EXAMPLE 5

Mycelium growth test
Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture:
  0.19 part by weight of dimethylformamide
  0.01 part by weight of emulsifier (alkylaryl polyglycol ether)
  1.80 parts by weight of water
Ratio of solvent mixture to nutrient medium:
  2 parts by weight of solvent mixture
  100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radical growth of the mycelium on the treated nutrient media was compared with the growth on the control nutrient medium. In the evaluation of the fungus growth, the following characteristic values were used:
  1 no fungus growth
  up to 3 very strong inhibition of growth
  up to 5 medium inhibition of growth
  up to 7 slight inhibition of growth
  9 growth equal to that of untreated control.

The active compounds, the active compound concentrations and the results can be seen from the following table:

The amount of active compound required for the desired active compound concentration in the spray liquor was mixed with the stated amount of the solvent and the concentrate was diluted with the stated amount of water, which contains the dispersing agent.

Plants of *Vicia faba* with 2 to 4 pairs of leaves were sprayed with the spray liquor until dripping wet. After 24 hours, 2 pairs of leaves were removed per plant and in each case placed in a Petri dish lined with moist blotting paper. Filter paper discs of 1 cm diameter were then dipped into an aqueous suspension of conidia of *Botrytis cinerea* and laid on the leaves. The dishes were closed. After an incubation time of 48 hours and an incubation temperature of 20° C., the necroses visible under the small discs were rated for frequency of occurrence. The ratings were converted to percent infection. 0% denoted no infection and 100% denoted that the plants were completely infected.

The active compounds, active compound concentrations and results can be seen from the table which follows:

TABLE 3

| Active compounds | *Botrytis* test (beans)/protective Infection in % at an active compound concentration of 0.025% |
|---|---|
| (B) | 66 |
| (1) | 1 |
| (5) | 16 |
| (3) | 14 |
| (2) | 42 |
| (8) | 29 |
| (9) | 30 |
| (17) | 35 |

EXAMPLE 6

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of

TABLE 2

| | | Mycelium growth test | | | | | | |
|---|---|---|---|---|---|---|---|---|
| Active compounds | Active compound concentration in ppm | Fungi | | | | | | |
| | | Fusarium culmorum | Fusarium nivale | Rhizoctonia solani | Pythium ultimum | Verticillium alboatrum | Pyricularia oryzae | Helminthosporium gramineum |
| (A) | 10 | 9 | 9 | 9 | 5 | 9 | 9 | 9 |
| (1) | 10 | 5 | 5 | 5 | 3 | 5 | 5 | 1 |
| (6) | 10 | 2 | 5 | 5 | 2 | 5 | 1 | 1 |
| (3) | 10 | 3 | 5 | 2 | 1 | — | 5 | 1 |
| (17) | 10 | 3 | 5 | 2 | 3 | — | — | 3 |
| (13) | 10 | 3 | 3 | 3 | 3 | — | 2 | 1 |
| (12) | 10 | 3 | 5 | 3 | 3 | — | 5 | 1 |
| (16) | 10 | 2 | 3 | 2 | 3 | 5 | 5 | 1 |

EXAMPLE 5

Botrytis test (beans)/protective
Solvent: 4.7 parts by weight of acetone
Dispersing agent: 0.3 part by weight of alkylaryl polyglycol ether
Water: 95.0 parts by weight emulsifier.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium* dendriticum) and incubated for 18 hours in a humidity chamber at 18°-20° C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

The active compounds, the concentrations of the active compounds and the results can be seen from the following table:

TABLE 4

| Fusicladium test (apple)/protective | |
|---|---|
| Active compound | Infection in % at an active compound concentration of 0.0025% |
| (B) | 91 |
| (5) | 22 |
| (7) | 40 |
| (3) | 46 |
| (2) | 32 |

It will be appreciated that the instant specification and examples are set forth by way of illustration and not limitation, and that various modifications and changes may be made without departing from the spirit and scope of the present invention.

What we claim is:

1. A method of combating fungi which damage crops which comprises applying to the fungi, to seed or to soil, a fungicidally effective amount of an α-(4-biphenyl)-benzyl-azolium salt of the formula

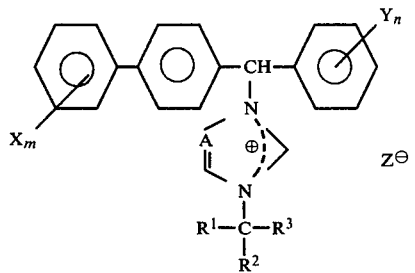

A is CH or N, $R^1$ and $R^2$ each independently is hydrogen, alkyl with 1 to 4 carbon atoms, or phenyl optionally substituted by fluoride, chlorine, bromine, alkyl with 1 to 6 carbon atoms, halogenoalkyl with 1 to 4 carbon atoms and up to 5 halogen atoms, alkoxy or alkylthio each with 1 to 4 carbon atoms, nitro or cyano, $R^3$ is phenyl, or phenylcarbonylalkyl with 1 to 4 carbon atoms in the alkyl moiety, the phenyl, phenylcarbonyl or phenylcarbonylalkyl radical being optionally substituted by fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro, cyano or phenyl which is itself optionally substituted by fluorine, chlorine, bromine, alkyl with 1 to 6 carbon atoms, halogenoalkyl with 1 to 4 carbon atoms and up to 5 halogen atoms, alkoxy or alkylthio each with 1 to 4 carbon atoms, nitro or cyano, m is 0, 1, 2, 3, 4 or 5, X each independently is halogen, alkyl with 1 to 6 carbon atoms, halogenoalkyl with 1 to 4 carbon atoms and up to 5 halogen atoms, alkoxy or alkylthio each with 1 to 4 carbon atoms, nitro or cyano.

n is 0, 1, 2, 3, 4 or 5,

Y each independently is halogen, alkyl with 1 to 6 carbon atoms, halogenoalkyl with 1 to 4 carbon atoms and up to 5 halogen atoms, alkoxy or alkylthio each with 1 to 4 carbon atoms, nitro, cyano or phenyl which is optionally substituted by halogen, alkyl with 1 to 6 carbon atoms, halogenoalkyl with 1 to 4 carbon atoms and up to 5 halogen atoms, alkoxy or alkylthio each with 1 to 4 carbon atoms, nitro or cyano, and Z is the anion of an inorganic or organic acid.

2. The method according to claim 1, in which

X each independently is fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano;

Y each independently is fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro, cyano or phenyl which is optionally substituted by fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano;

$R^1$ and $R^2$ each independently is hydrogen, alkyl with 1 to 4 carbon atoms, or phenyl which is optionally substituted by fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano;

$R^3$ is phenyl, phenylcarbonyl or phenylcarbonylalkyl with 1 to 4 carbon atoms in the alkyl moiety each optionally substituted by fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro, cyano or phenyl which is itself optionally substituted by fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano;

m and n each is 0, 1, 2 or 3; and

Z is a fluoride, chloride, bromide, iodide, nitrate, sulphate, phosphate, acetate, propionate, glycolate, lactate, malonate, succinate, maleate, fumarate, tartrate, citrate, benzoate, methylsulphonate, ethylsulphonate, p-toluenesulphonate, benzenesulphonate or salicylate anion.

3. The method according to claim 1, in which the active compound is applied to the habitat which is seed, in an amount of 0.001 to 50 g per kg of seed.

4. The method according to claim 1, in which the active compound is 1,3-bis-[α-(4-biphenylyl)-benzyl]-imidazolium chloride of the formula

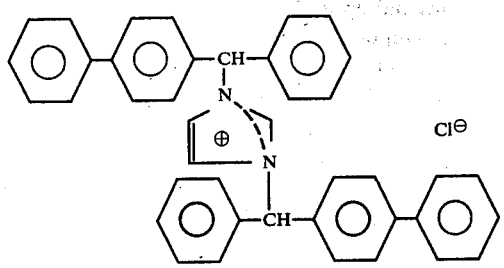
Cl⊖
5. The method of claim 1, in which the active compound is 1,3-bis-[α-(4-biphenylyl)-benzyl]-imidazolium nitrate of the formula
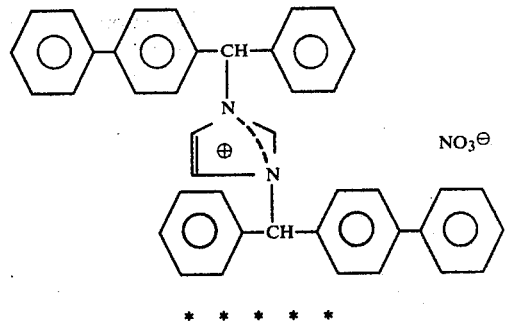
* * * * *

Disclaimer

4,251,540.—*Erik Regel; Wilfried Draber and Karl H. Buchel, Wuppertal, Peter Kraus, Koeln, and Wilhelm Brandes, Leichlingen,* All of Fed. Rep. of Germany. COMBATING CROP DAMAGING FUNGI WITH ALPHA-(4-BIPHENYLYL)-BENZYL-AZOLIUM SALTS. Patent dated Feb. 17, 1981. Disclaimer filed Mar. 5, 1981, by the assignee, *Bayer Aktiengesellschaft.*

The term of this patent subsequent to Jan. 6, 1998, has been disclaimed.

[*Official Gazette Sept. 15, 1981.*]